(12) United States Patent
Lin et al.

(10) Patent No.: US 9,115,116 B2
(45) Date of Patent: Aug. 25, 2015

(54) DUAL ACTION INHIBITORS AGAINST HISTONE DEACETYLASES AND 3-HYDROXY-3-METHYLGLUTARYL COENZYME A REDUCTASE

(71) Applicants: Academia Sinica, Taipei (TW); National Taiwan University, Taipei (TW)

(72) Inventors: Jung-Hsin Lin, New Taipei (TW); Ching-Chow Chen, Taipei (TW); Jim-Min Fang, Taipei (TW); Jhih-Bin Chen, Lukang Township, Changhua County (TW); Ting-Rong Chern, Taipei (TW); Tzu-Tang Wei, Taipei (TW)

(73) Assignees: Academia Sinica, Taipei (TW); National Taiwan University, Taipei (TW)

( * ) Notice: Subject to any disclaimer, the term of this patent is extended or adjusted under 35 U.S.C. 154(b) by 0 days.

(21) Appl. No.: 14/160,515

(22) Filed: Jan. 21, 2014

(65) Prior Publication Data

US 2014/0206645 A1 Jul. 24, 2014

Related U.S. Application Data

(60) Provisional application No. 61/756,453, filed on Jan. 24, 2013.

(51) Int. Cl.

| | |
|---|---|
| *C07D 207/32* | (2006.01) |
| *C07D 309/10* | (2006.01) |
| *A61K 31/4192* | (2006.01) |
| *A61K 31/351* | (2006.01) |
| *C07D 405/12* | (2006.01) |
| *C07D 309/30* | (2006.01) |
| *C07F 7/18* | (2006.01) |

(52) U.S. Cl.
CPC ............ *C07D 405/12* (2013.01); *C07D 309/30* (2013.01); *C07F 7/1856* (2013.01)

(58) Field of Classification Search
CPC ............. A61K 31/4192; A61K 31/351; C07D 207/32; C07D 309/10
See application file for complete search history.

(56) References Cited

PUBLICATIONS

Kazantsev, 2008, Nature Reviews, Drug Discovery, vol. 7, p. 854-868.*
Chen et al, 2013, J. Med. Chem. vol. 56, p. 3645-3655.*

* cited by examiner

*Primary Examiner* — Rebecca Anderson
*Assistant Examiner* — Karen Cheng
(74) *Attorney, Agent, or Firm* — Chih Feng Yeh; Huntington IP consulting Co., Ltd.

(57) ABSTRACT

Disclosed herein are novel compounds of formula (I), and uses thereof. The compounds of Formula (I) are inhibitors of histone deacetylases (HDACs) and 3-hydroxy-3-methylglutaryl coenzyme A (HMG-CoA) reductase (HMGR). Also provided are methods of using the compounds of Formula (I) for inhibiting the activity of HDACs and HMGR, treating diseases associated with HDACs or HMGR (e.g., cancer, hypercholesterolemia, an acute or chronic inflammatory disease, autoimmune disease, allergic disease, pathogen infection, neurodegenerative disease, or a disease associated with oxidative stress, (I)

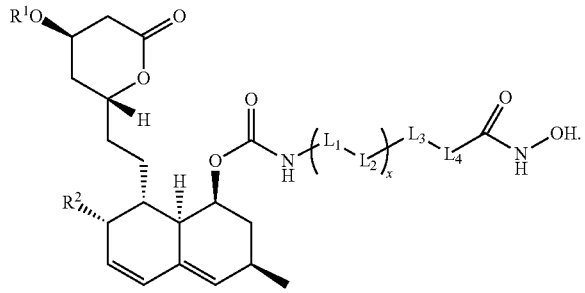

2 Claims, 1 Drawing Sheet

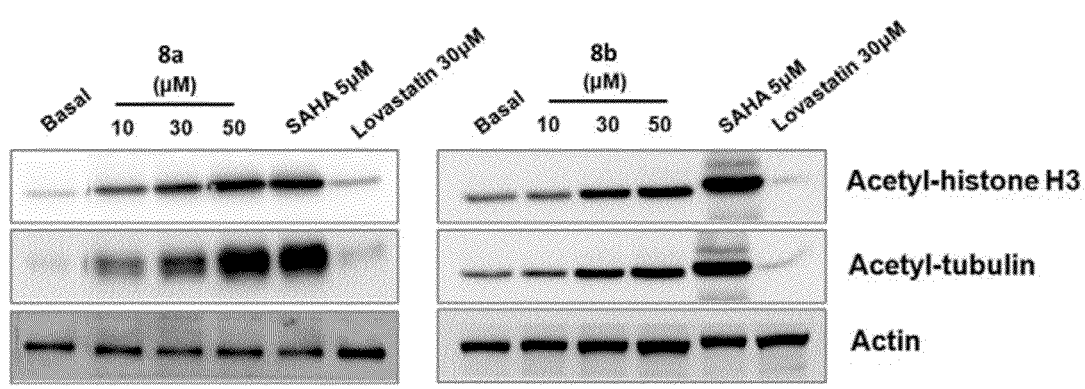

DUAL ACTION INHIBITORS AGAINST HISTONE DEACETYLASES AND 3-HYDROXY-3-METHYLGLUTARYL COENZYME A REDUCTASE

CROSS-REFERENCE TO RELATED APPLICATION

This application claims the benefit of U.S. Provisional Application No. 61/756,453, filed Jan. 24, 2013.

BACKGROUND OF RELATED ART

1. Technical Field

The present disclosure relates to the treatment of cancer. More particularly, the disclosed invention relates to the use of novel bi-functional inhibitors against histone deacetylases (HDACs) and 3-hydroxy-3-methylglutaryl coenzyme A (HMG-CoA) reductase (HMGR), and theirs uses as medicaments for the treatment or prophylaxis of diseases and/or conditions associated with inhibition and/or suppression of HDACs and HMGR, such as cancers.

2. Description of Related Art

Acetylation and deacetylation of histones are carried out by histone acetyl transferases (HAT) and histone deacetylases (HDACs). The state of acetylation of histones is an important determinant of gene transcription. Deacetylation is generally associated with reduced transcription of genes whereas increased acetylation of histones as induced by the action of HDAC inhibitors (HDACi) results in greater transcription of genes. Thus, HDAC inhibitors affect multiple processes in the cell which are likely to depend upon the dynamic state of the cell with respect to its capabilities of replication and differentiation.

In another aspect, statins have recently been shown to be effective for cancer prevention in observational, preclinical, and certain randomized controlled studies. Statins, such as lovastatin and mevastatin, are known to reduce serum cholesterol levels through competitive inhibition at 3-hydroxy-3-methylglutaryl coenzyme A reductase (HMGR). The HMGR inhibitors (HMGRi) have been used to decrease the incidence of cardiovascular and cerebrovascular disorders, and to prevent cardiovascular disease (CVD). Statins possess an established record of safety and efficacy in human CVD prevention.

It has been reported that the combination use of anticancer agents with statins may reduce side effects to attain better treatment of cancers. Furthermore, the in vitro experiment using combination of HDACi and HMGRi exhibited a synergistic induction on apoptosis of HeLa cells.

Given the prior knowledge relating to HDACi and HMGRi, inventors of the present disclosure conceived that concurrent inhibition of HDAC and HMGR would be a promising approach for cancer treatment. However, using multi-component drug-cocktails for therapeutics has some drawbacks, such as complex pharmacokinetics, unpredictable drug-drug interaction, and formulation problems due to different solubilities of individual drugs. Alternatively, to design a single compound that simultaneously modulates multiple targets, dubbed designed multiple ligand (DML), has become an emerging paradigm for drug discovery. DMLs constructed by incorporation of HDACi into other active agents targeting inosine monophosphate dehydrogenase, (Chen, L., et al. *J. Med. Chem.* 2007, 50, 6685. Chen, L., et al. *Bioorg. Med. Chem.* 2010, 18, 5950.) nuclear vitamin D receptor, (Tavera-Mendoza, L. E., et al. *Proc. Natl. Acad. Sci. U.S.A.* 2008, 105, 8250.) tyrosine kinase receptor (Mahboobi, S., et al. *J. Med. Chem.* 2009, 52, 2265. Cai, X., et al. *J. Med. Chem.* 2010, 53, 2000.) or topoisomerase II (Guerrant, W., et al. *J. Med. Chem.* 2012, 55, 1465.) have been tested in cancer treatments. (O'Boyle, N. M. & Meegan, M. J. *Curr. Med. Chem.* 2011, 18, 4722.)

Therefore, it is the aim of the present disclosure to provide novel dual-action compounds that target both HDACs and HMGRs. These compounds are thus potential lead compounds for preparing or manufacturing medicaments to prevent or treat various diseases and conditions, in which suppression of HDACs and HMGRs provides beneficial outcomes.

SUMMARY

The following presents a simplified summary of the disclosure in order to provide a basic understanding to the reader. This summary is not an extensive overview of the disclosure and it does not identify key/critical elements of the present invention or delineate the scope of the present invention. Its sole purpose is to present some concepts disclosed herein in a simplified form as a prelude to the more detailed description that is presented later.

The present disclosure is based, at least in part, on the discovery that certain hexanohydroxamic acid derivatives are potent inhibitors of HDACs and HMGRs and are thus potential lead compounds for manufacturing a medicament for treating disease and/or condition associated with inhibition and/or suppression of HDACs and HMGRs, including cancers.

In one aspect, the present disclosure provides a compound of formula (I),

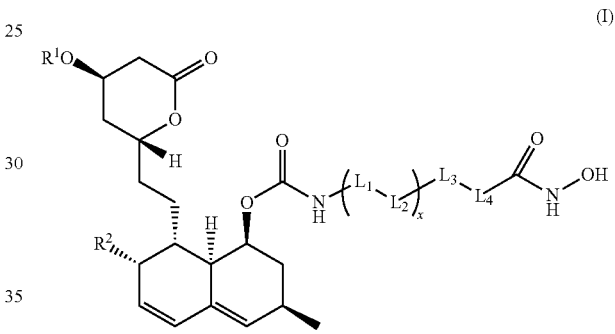

(I)

or its pharmaceutically acceptable salt, solvate, derivative or prodrug, wherein:

x is an integral from 1 to 3;

$L_1$ is ethylene;

$L_2$ is independently carbon or oxygen; or $L_1$ and $L_2$ together are deleted;

$L_3$ is 4-phenyl-1,2,3-triazolyl, provided that $L_2$ is carbon, and x is 1; or $L_1$ and $L_2$ together are deleted;

$L_4$ is null or $C_{1-9}$ alkylene, provided that $L_1$ is ethylene, $L_2$ is oxygen, when $L_4$ is null;

$R^1$ is H, aralkyl or alkylsilyl; and $R^2$ is H or alkyl.

In certain embodiments, the compound of formula (I) can be a compound of formula (II) or its pharmaceutically acceptable salt, solvate, derivative or prodrug:

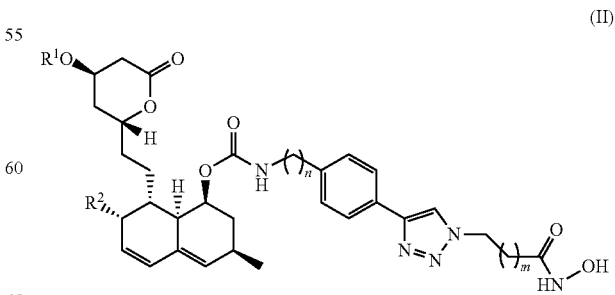

(II)

wherein:

n is an integer from 0 to 3; and m is an integer from 0 to 9.

In certain embodiments, the compound of formula (II) is selected from the group consisting of,
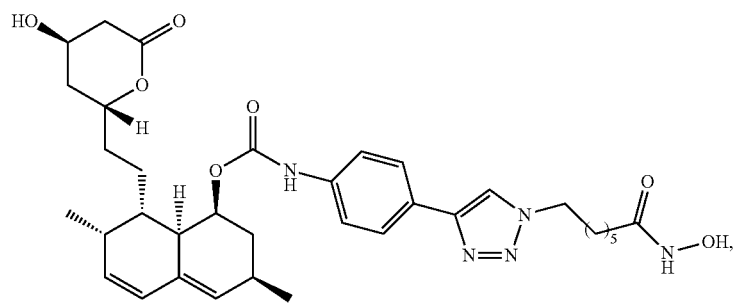
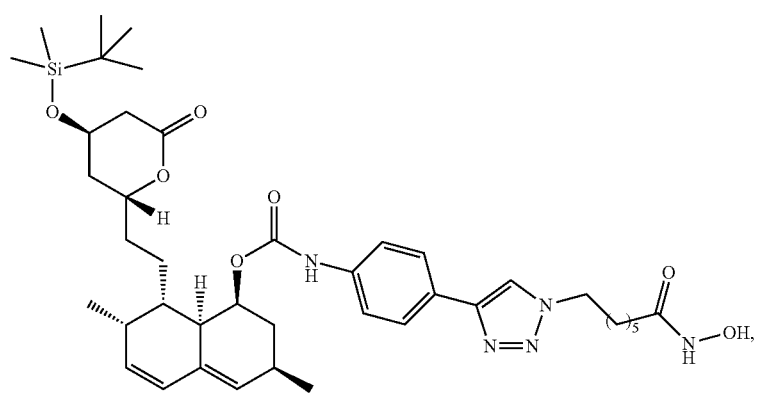
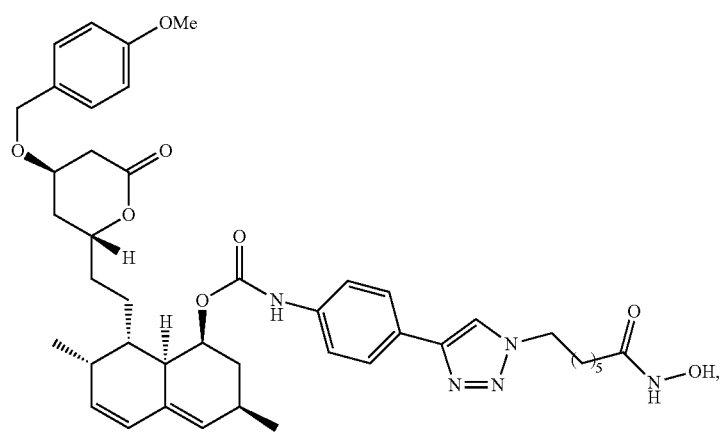
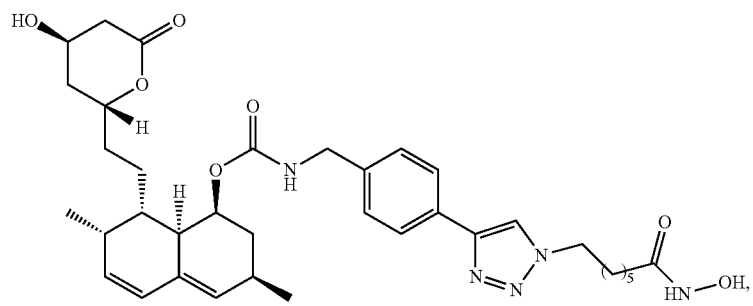

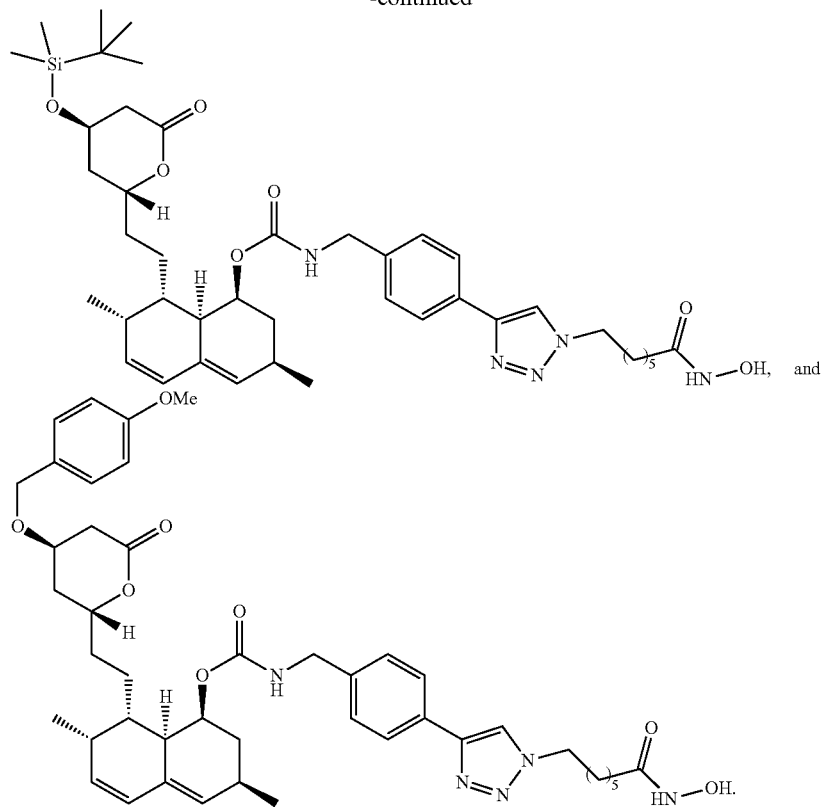
In other embodiments, the compound of formula (I) can be a compound of formula (III), or its pharmaceutically acceptable salt, solvate, derivative or prodrug:
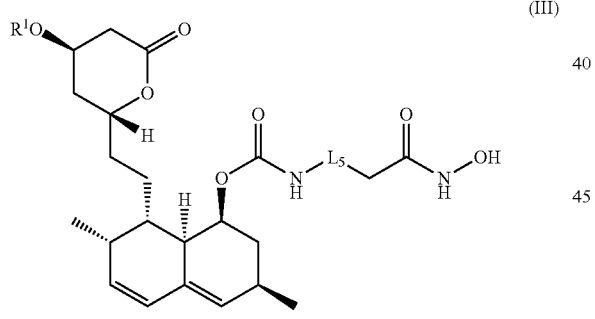
(III)
wherein $L_5$ is $—(CH_2)_x—$, or $—(CH_2CH_2O)_y—$; x is an integer from 0 to 9, and y is an integer from 1 to 3.
In certain embodiments, the compound of formula (III) is selected from the group consisting of,
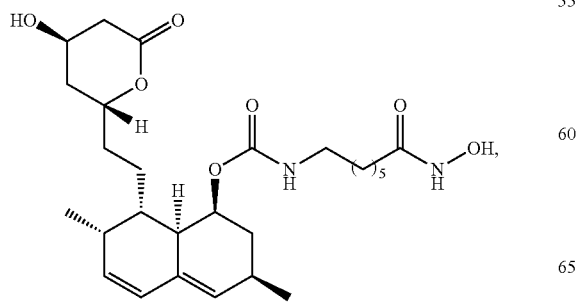
-continued
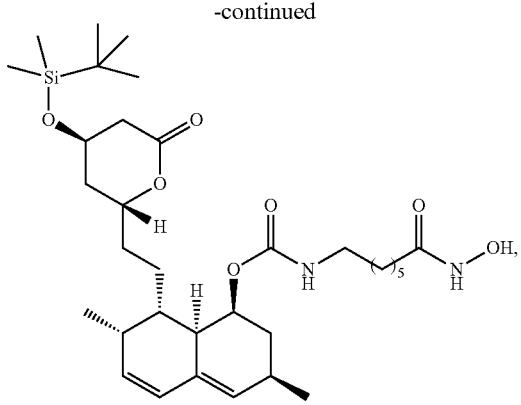
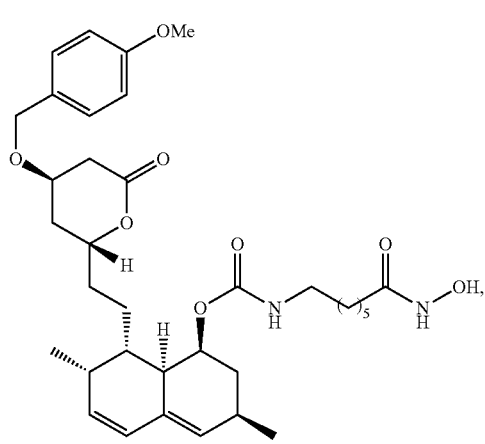

-continued

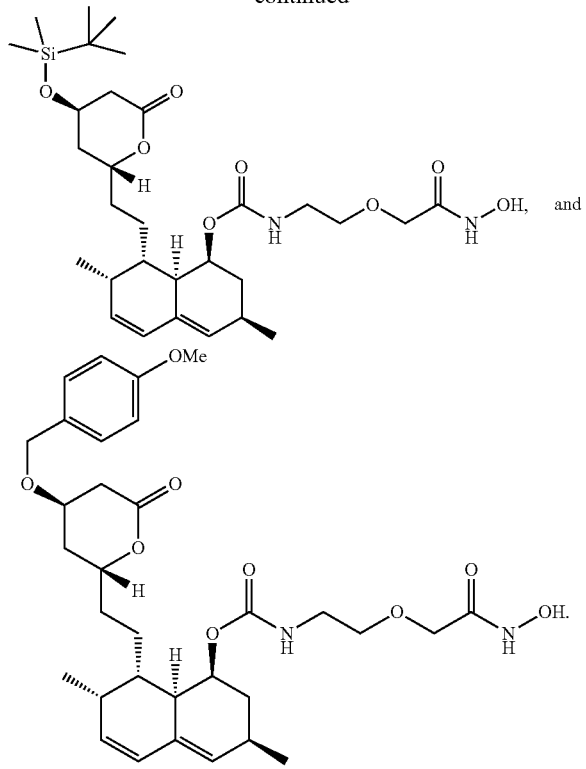

Another aspect of the present invention relates to pharmaceutical compositions for treating cancers comprising an effective amount of the compound described above, its pharmaceutically acceptable salt, solvate, derivative or prodrug; and a pharmaceutically acceptable carrier.

In a further aspect, the present disclosure relates to a method of treating cancer, hypercholesterolemia, an acute or chronic inflammatory disease, autoimmune disease, allergic disease, pathogen infection, neurodegenerative disease, or a disease associated with oxidative stress. The method includes the step of, administering to a subject an effective amount of one or more compounds described above, or the pharmaceutical composition described herein.

In certain embodiments, the cancer can be leukemia, Hodgkin's disease, lymphoma, Ewing's sarcoma, multiple myeloma, Wilms' tumor, bone tumor, neuroblastoma, retinoblastoma, testicular cancer, thyroid cancer, prostate cancer, larynx cancer, cervical cancer, nasopharynx cancer, breast cancer, colon cancer, pancreatic cancer, head and neck cancer, esophageal cancer, rectal cancer, small-cell lung cancer, non-small-cell lung cancer, brain cancer, melanoma, skin cancers other than melanoma, or CNS neoplasm.

In certain embodiments, the subject being treated by the method described herein can be a human, such as a human patient having, suspected of having, or at risk for the target disease as described herein.

Many of the attendant features and advantages of the present disclosure will become better understood with reference to the following detailed description.

BRIEF DESCRIPTION OF THE DRAWINGS

These and other features, aspects and advantages of the present invention will become better understood with reference to the following description, appended claims and the accompanying drawings, where:

FIG. 1 is the Western blot analysis illustrating the effects of the compound (8a) and (8b) on acetylation of histone H3 in A549 lung cancer cells in accordance with one embodiment of the present invention.

DETAILED DESCRIPTION

The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

For convenience, certain terms employed in the specification, examples and appended claims are collected here. Unless defined otherwise, all technical and scientific terms used herein have the same meaning as commonly understood by one of the ordinary skill in the art to which the present disclosure belongs.

Unless otherwise required by context, it will be understood that singular terms shall include plural forms of the same and plural terms shall include the singular. Specifically, as used herein and in the claims, the singular forms "a" and "an" include the plural reference unless the context clearly indicates otherwise. Also, as used herein and in the claims, the terms "at least one" and "one or more" have the same meaning and include one, two, three, or more.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in the respective testing measurements. Also, as used herein, the term "about" generally means within 10%, 5%, 1%, or 0.5% of a given value or range. Alternatively, the term "about" means within an acceptable standard error of the mean when considered by one of ordinary skill in the art. Other than in the operating/working examples, or unless otherwise expressly specified, all of the numerical ranges, amounts, values and percentages such as those for quantities of materials, durations of times, temperatures, operating conditions, ratios of amounts, and the likes thereof disclosed herein should be understood as modified in all instances by the term "about." Accordingly, unless indicated to the contrary, the numerical parameters set forth in the present disclosure and attached claims are approximations that can vary as desired. At the very least, each numerical parameter should at least be construed in light of the number of reported significant digits and by applying ordinary rounding techniques.

When a range of values is listed, it is intended to encompass each value and sub-range within the range. For example "$C_{1-9}$" is intended to encompass, $C_1$, $C_2$, $C_3$, $C_4$, $C_5$, $C_6$, $C_7$, $C_8$, $C_9$, $C_{1-9}$, $C_{1-8}$, $C_{1-7}$, $C_{1-6}$, $C_{1-5}$, $C_{1-4}$, $C_{1-3}$, $C_{1-2}$, $C_{2-9}$, $C_{2-8}$, $C_{2-7}$, $C_{2-6}$, $C_{2-5}$, $C_{2-4}$, $C_{2-3}$, $C_{3-9}$, $C_{3-8}$, $C_{3-7}$, $C_{3-6}$, $C_{3-5}$, $C_{3-4}$, $C_{4-9}$, $C_{4-8}$, $C_{4-7}$, $C_{4-6}$, $C_{4-5}$, $C_{5-9}$, $C_{5-8}$, $C_{5-7}$, $C_{5-6}$, $C_{6-9}$, $C_{6-8}$, $C_{6-7}$, $C_{7-9}$, $C_{7-8}$, and $C_{8-9}$.

The term "alkyl" includes substituted and unsubstituted straight, branched and cyclic alkyl groups.

The term "aryl" refers to a radical of a monocyclic aromatic ring system having 6-14 ring carbon atoms and zero heteroatoms provided in the aromatic ring system. In certain embodiments, aryl refers to an aromatic ring system having 6 carbon atoms in the aromatic ring ("$C_6$ aryl", e.g., phenyl). Unless otherwise specified, each instance of an aryl group is independently optionally substituted, i.e., unsubstituted (an "unsubstituted aryl") or substituted (a "substituted aryl") with one or more substituents. In certain embodiments, the aryl group is unsubstituted $C_6$ aryl. In certain embodiments, the aryl group is substituted $C_6$ aryl.

The term "aralkyl" is a subset of alkyl and aryl, as defined herein, and refers to an optionally substituted alkyl group substituted by an optionally substituted aryl group. In certain embodiments, the aralkyl is optionally substituted benzyl. In certain embodiments, the aralkyl is benzyl.

The term "silyl" refers to a moiety of the formula: —Si($R_1$)($R_2$)($R_3$), wherein each $R_1$, $R_2$, and $R_3$ are independently H, alkyl, alkenyl, alkyne, or aryl substituent described herein.

Alkyl, aryl, and aralkyl as defined herein are divalent bridging groups obtained by removing two hydrogen atoms therefrom and are further referred to as alkylene, arylene, and aralkylene. For example, an "alkylene" is positioned between two other chemical groups and serves to connect them. An example of an alkylene group is —($CH_2$)$_n$—. The term "arylene" refers to a bidentate aryl group that bonds to two other groups and serves to connect these groups, e.g.,

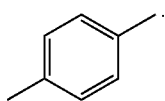

Further, alkyl, aryl, and aralkyl as defined herein are optionally substituted.

The term "prodrug" as used herein, refers to any compound that when administered to a biological system yields the "drug" substance either as a result of spontaneous chemical reaction(s) or by enzyme catalyzed or metabolic reaction(s).

The term "treating" encompasses partially or completely preventing, ameliorating, mitigating and/or managing a symptom, a secondary disorder or a condition associated with HDACs and HMGRs, in which suppression or inhibition of HDACs and HMGRs provides a benefit to the subject having or suspected of having such symptom, disorder or condition. The term "treating" as used herein refers to application or administration of one or more compounds of the present disclosure to a subject, who has a symptom, a secondary disorder or a condition associated with HDACs and HMGRs, with the purpose to partially or completely alleviate, ameliorate, relieve, delay onset of, inhibit progression of, reduce severity of, and/or reduce incidence of one or more symptoms, secondary disorders or features associated with HDACs and HMGRs. Symptoms, secondary disorders, and/or conditions associated with HDACs and HMGRs include, but are not limited to, cancer, hypercholesterolemia, an acute or chronic inflammatory disease, autoimmune disease, allergic disease, pathogen infection, neurodegenerative disease, or a disease associated with oxidative stress. Treatment may be administered to a subject who exhibits only early signs of such symptoms, disorder, and/or condition for the purpose of decreasing the risk of developing the symptoms, secondary disorders, and/or conditions associated with HDACs and HMGRs. Treatment is generally "effective" if one or more symptoms or clinical markers are reduced as that term is defined herein. Alternatively, a treatment is "effective" if the progression of a symptom, disorder or condition is reduced or halted.

The term "effective amount" as used herein refers to the quantity of a component or medicament which is sufficient to yield a desired "effective treatment" as defined hereinabove.

The specific therapeutically effective amount will vary with factors such as the particular condition being treated, the physical condition of the patient (e.g., the patient's body mass, age, or gender), the type of mammal or animal being treated, the duration of the treatment, the nature of concurrent therapy (if any), and the specific formulations employed. An effective amount is also one in which any toxic or detrimental effects of the compound or composition are outweighed by the therapeutically beneficial effects. Effective amount may be expressed, for example, as the total mass of the medicament (e.g., in grams, milligrams or micrograms) or a ratio of mass of the medicament to body mass, e.g., as milligrams per kilogram (mg/kg). Persons having ordinary skills could calculate the human equivalent dose (HED) for the medicament (such as the compounds of the present disclosure) based on the doses determined from animal models. For example, one may follow the guidance for industry published by US Food and Drug Administration (FDA) entitled "Estimating the Maximum Safe Starting Dose in Initial Clinical Trials for Therapeutics in Adult Healthy Volunteers" in estimating a maximum safe dosage for use in human subjects.

The term "subject" refers to an animal including the human species that is treatable with the compounds of the present disclosure. The term "subject" is intended to refer to both the male and female gender unless one gender is specifically indicated, and may be any age, e.g., a child or adult.

The subject invention provides compounds of formula (I), compositions comprising the compounds of formula (I), and therapeutically uses of compound of formula (I):

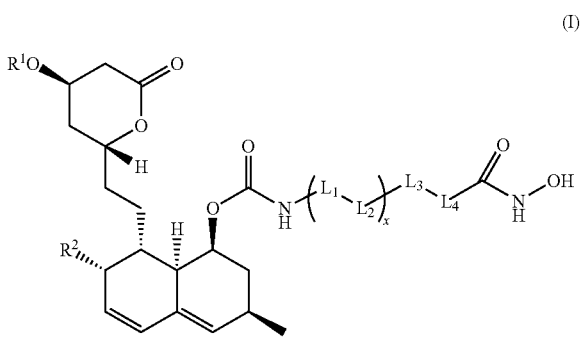

(I)

wherein:
x is an integral from 1 to 3;
$L_1$ is ethylene, and $L_2$ is independently carbon or oxygen; or $L_1$ and $L_2$ together are deleted;
$L_3$ is 4-phenyl-1,2,3-triazolyl, provided that $L_2$ is carbon, and x is 1; or $L_1$ and $L_2$ together are deleted;
$L_4$ is null or $C_{1-9}$ alkylene, provided that $L_1$ is ethylene, $L_2$ is oxygen, when $L_4$ is null;
$R^1$ is H, aralkyl or alkylsilyl; and
$R^2$ is H or alkyl.

Additionally, salts, solvates, derivatives and prodrugs of the compounds of formula (I) also are included in the present disclosure and can be used in the composition and/or methods disclosed herein. The present disclosure further includes all possible stereoisomers and geometric isomers of the compounds of formula (I). The present invention includes both racemic compounds and optically active isomers. When a compound of formula (I) is desired as a single enantiomer, it can be obtained either by resolution of the final product or by stereospecific synthesis from either isomerically pure starting material or use of a chiral auxiliary reagent. Resolution of the final product, an intermediate, or a starting material can be achieved by any suitable method known in the art. Additionally, in situations where tautomers of the compounds of formula (I) are possible, the present disclosure is intended to include all tautomeric forms of the compounds. Prodrugs of compounds of formula (I) also are included in the present disclosure. It is well established that a prodrug approach, wherein a compound is derivatized into a form suitable for formulation and/or administration, then released as a drug in vivo, has been successfully employed to transiently (e.g., bioreversibly) after the physicochemical properties of the compound. Suitable prodrugs include, for example, acid derivatives, such as amides and esters.

Compounds of the present disclosure can also exist as salts. Pharmaceutically acceptable salts of the present disclosure often are preferred in the methods of the invention. Salts of compounds of formula (I) can be prepared during the final isolation and purification of the compounds or separately by reacting the compound with an acid having a suitable cation. The pharmaceutically acceptable salts of compounds of formula (I) can be acid addition salts formed with pharmaceutically acceptable acids. Examples of acids which can be employed to form pharmaceutically acceptable salts include inorganic acids such as nitric, boric, hydrochloric, hydrobromic, sulfuric, and phosphoric, and organic acids such as oxalic, maleic, succinic, tartaric, and citric. Non-limiting examples of salts of compounds of the invention include, but are no limited to, the hydrochloride, hydrobromide, hydroiodide, sulfate, bisulfate, 2-hydroxyethansulfonate, phosphate, hydrogen phosphate, acetate, adipate, alginate, aspartate, benzoate, bisulfate, butyrate, camphorate, camphorsulfonate, digluconate, glycerolphosphate, hemisulfate, heptanoate, hexanoate, formate, succinate, fumarate, maleate, ascorbate, isethionate, salicylate, methanesulfonate, mesitylenesulfonate, naphthylenesulfonate, nicotinate, 2-naphthalenesulfonate, oxalate, pamoate, pectinate, persulfate, 3-phenylproprionate, picrate, pivalate, propionate, trichloroacetate, trifluoroacetate, phosphate, glutamate, bicarbonate, paratoluenesulfonate, undecanoate, lactate, citrate, tartrate, gluconate, methanesulfonate, ethanedisulfonate, benzene sulphonate, and p-toluenesulfonate salts. In addition, available amino groups present in the compounds of the invention can be quaternized with methyl, ethyl, propyl, and butyl chlorides, bromides, and iodides; dimethyl, diethyl, dibutyl, and diamyl sulfates; decyl, lauryl, myristyl, and stearyl chlorides, bromides, and iodides; and benzyl and phenethyl bromides. In light of the foregoing, any reference to compounds of formula (I) appeared herein is intended to include compounds of formula (I) as well as pharmaceutically acceptable salts, solvates, or prodrugs thereof.

The compounds of formula (I) are dual function inhibitors that suppress the actions of HDAC and HMGR, hence are potential lead compounds for manufacturing a medicament for treating a disease or condition, in which suppression or inhibition of HDACs and HMGRs provides benefits. Applicable disease or condition includes, but is not limited to, cancer, hypercholesterolemia, an acute or chronic inflammatory disease, autoimmune disease, allergic disease, pathogen infection, neurodegenerative disease, or a disease associated with oxidative stress.

In certain embodiments, the compound of formula (I) can be a compound of formula (II):

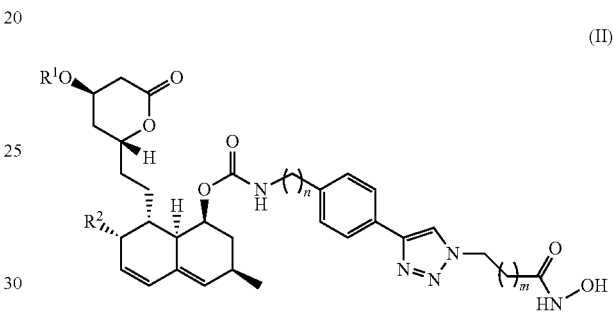

wherein:
n is an integer from 0 to 3; and m is an integer from 0 to 9;
or its pharmaceutically acceptable salt, solvate, derivative or prodrug.

Specifically, the compound of formula (II) is selected from the group consisting of:

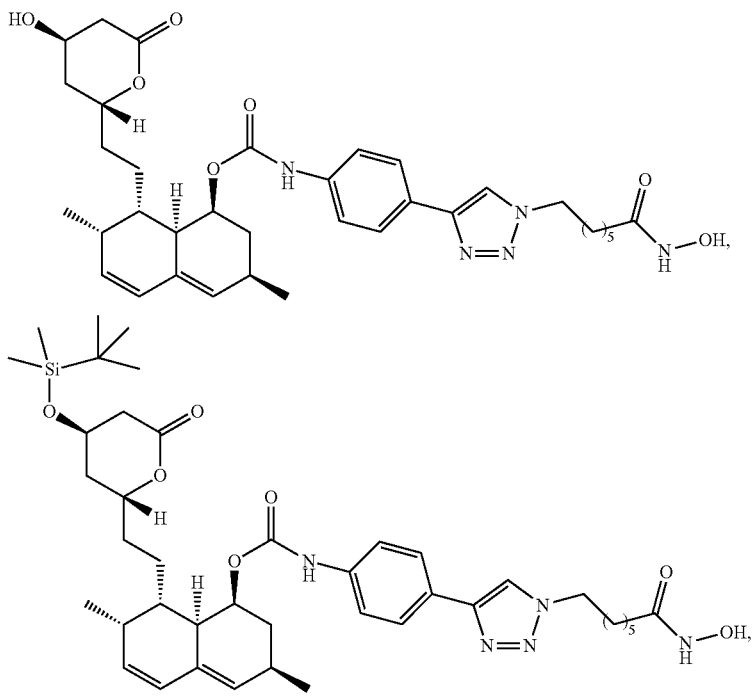

-continued
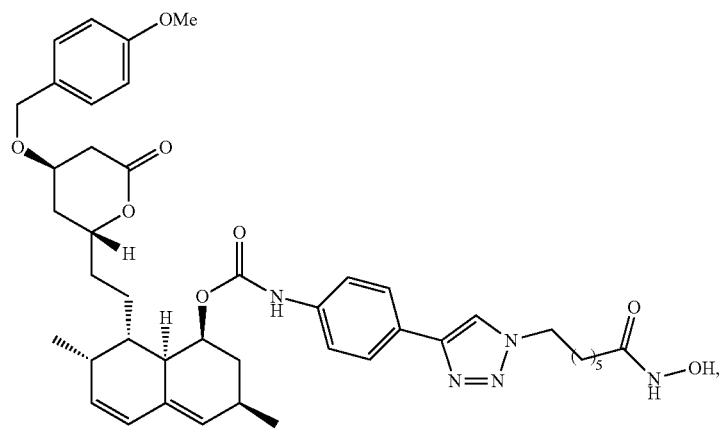
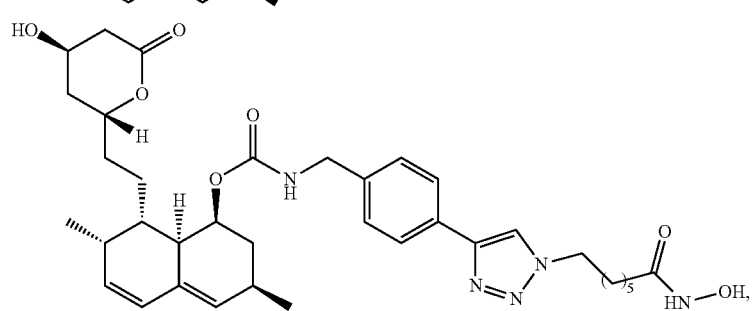
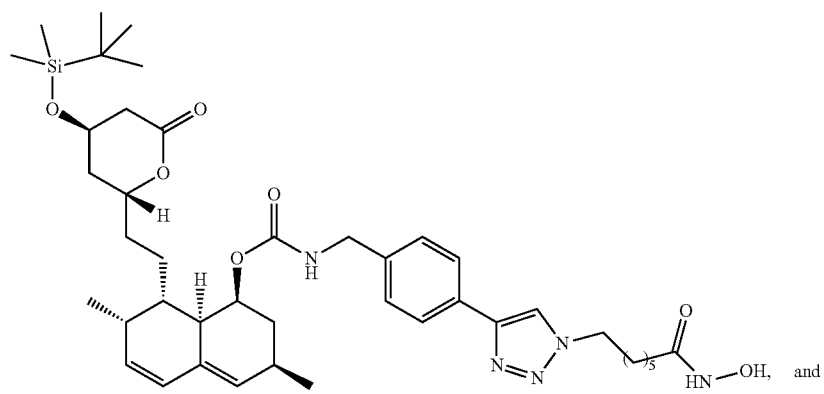 and
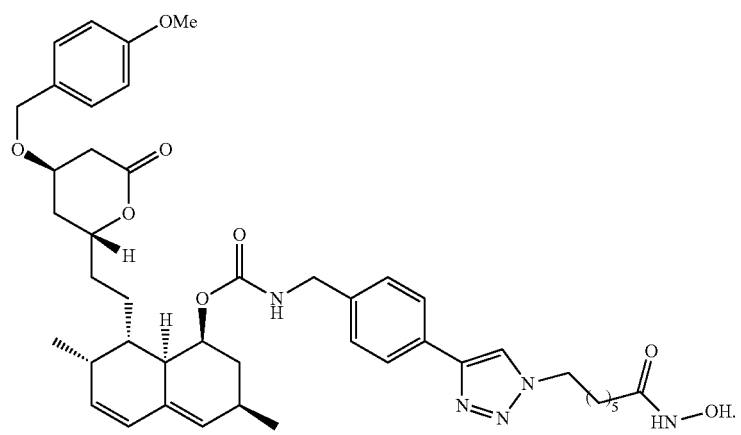

In other embodiments, the compound of formula (I) can be a compound of formula (III):

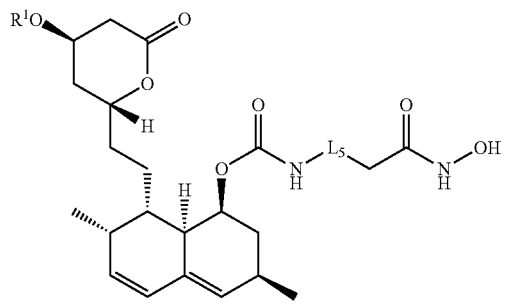

wherein $L_5$ is —$(CH_2)_x$—, or —$(CH_2CH_2O)_y$—; x is an integer from 0 to 9, and y is an integer from 1 to 3;

or its pharmaceutically acceptable salt, solvate, derivative or prodrug.

Specifically, the compound of formula (III) is selected from the group consisting of:

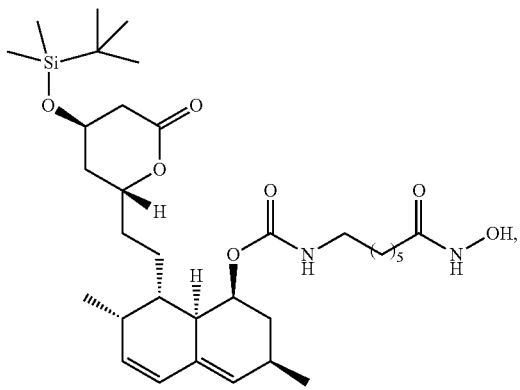

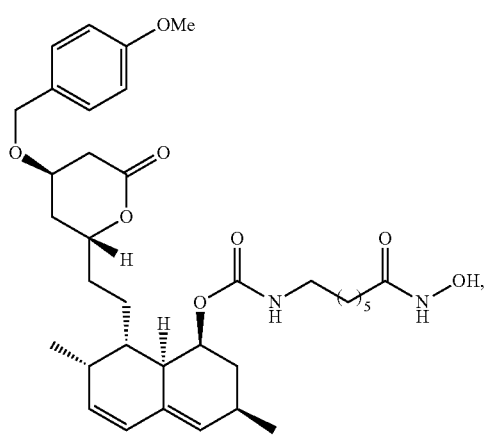

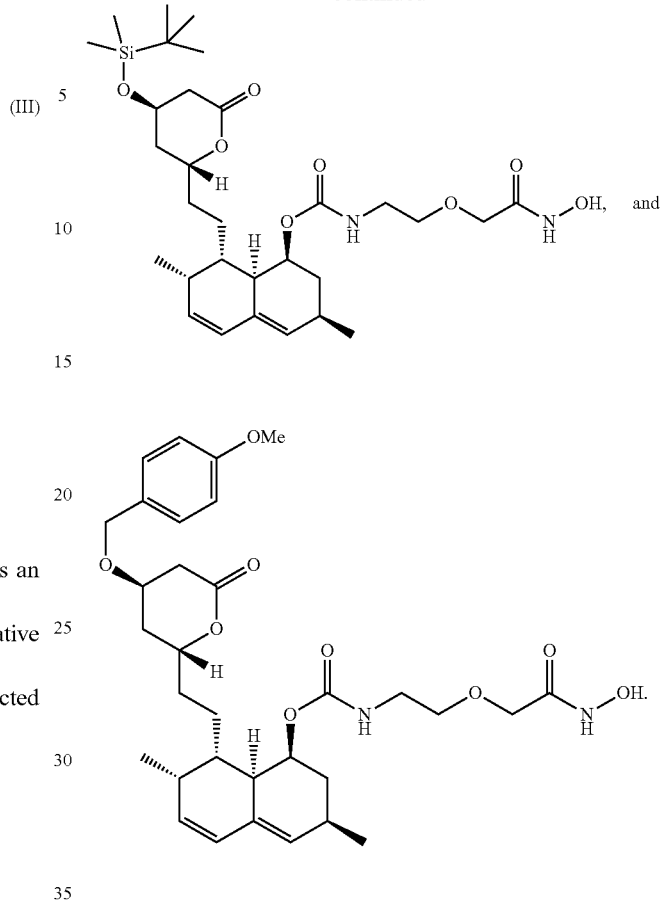

The following synthetic schemes are representative of the reactions used to synthesize compounds of formula W. Modifications and alternate schemes to prepare compounds of the present disclosure are readily within the capabilities of persons skilled in the art.

In general, compounds of formula (I) can be prepared by any suitable method known in the art, or by the following processes which form part of the present invention. It should be understood that protecting groups can be utilized in accordance with general principles of synthetic organic chemistry to provide compounds of structural formula (I). Protecting group-forming reagents are well known to persons skilled in the art, these protecting groups are removed when necessary by appropriate basic, acidic, or hydrogenolytic conditions known to persons skilled in the art. Accordingly, compounds of formula (I) not specifically exemplified herein can be prepared by persons skilled in the art.

$^1$H NMR and $^{13}$C NMR spectra were recorded on a spectrometer with TMS as an internal standard. Standard abbreviation indicating multiplicity was used as follows: s=singlet, d=doublet, t=triplet, q=quadruplet, m=multiplet and br=broad. The progress of all reactions was monitored by TLC on pre-coated silica gel plates, Column chromatography was performed using silica gel unless otherwise indicated.

In certain embodiments, compounds of formula (II) can be prepared according to the following synthetic scheme 1.

Scheme 1
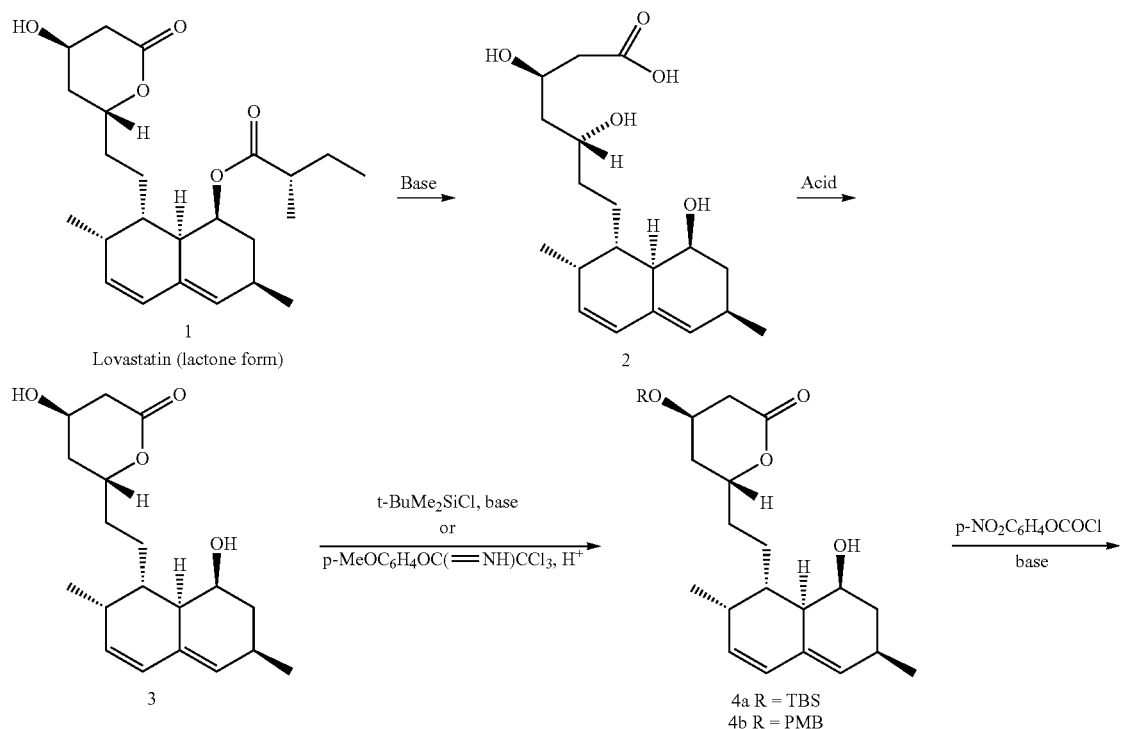
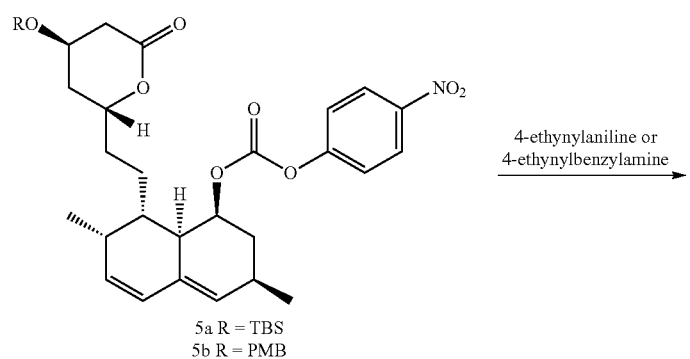
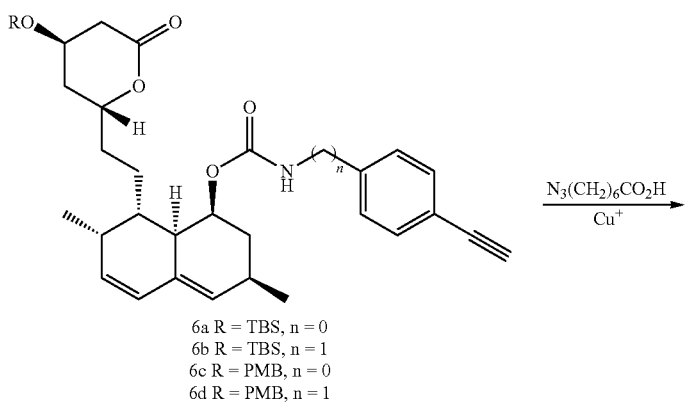

-continued

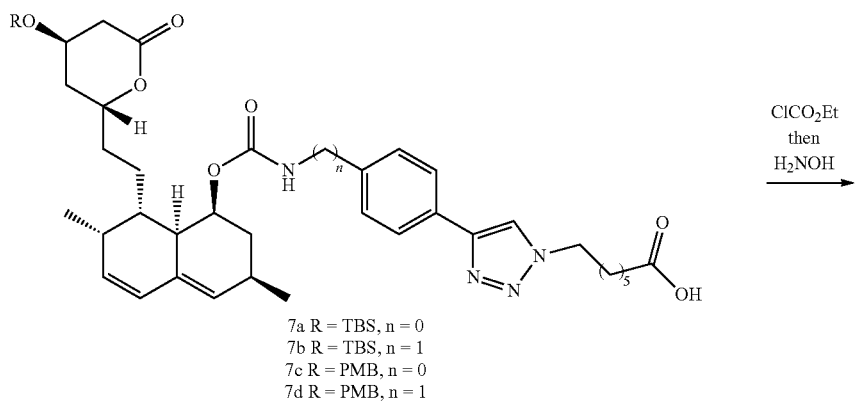

7a R = TBS, n = 0
7b R = TBS, n = 1
7c R = PMB, n = 0
7d R = PMB, n = 1

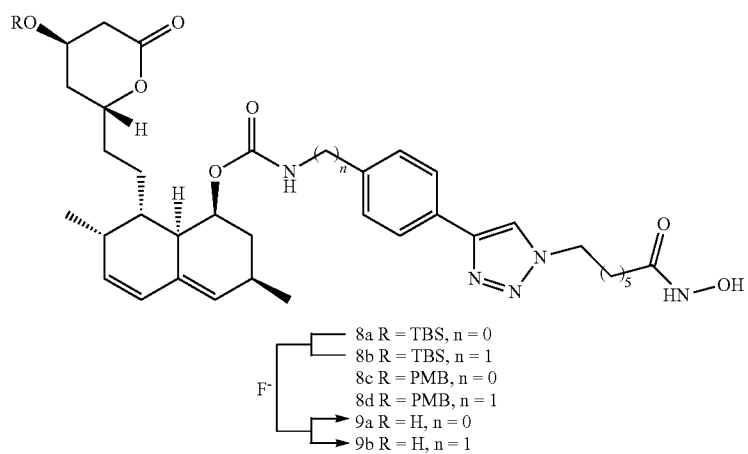

8a R = TBS, n = 0
8b R = TBS, n = 1
8c R = PMB, n = 0
8d R = PMB, n = 1
9a R = H, n = 0
9b R = H, n = 1

Specifically, the synthetic method as depicted in scheme 1 includes steps of:

(i) treating statin, e.g., lovastatin (in the lactone form 1) with a base to prepare an intermediate compound (2) by opening of the lactone ring and cleavage of the ester bond;

(ii) treating compound (2) with a mineral acid to form a lactone compound (3);

(iii) protecting compound (3) with suitable protecting group to produce dimethyl-tert-butylsilyl ether (4a) or ρ-methoxybenzyl ether (4b);

(iv) reacting compound (4a) with ρ-nitrophenyl chloroformate to form a carbonate compound (5a), in which TBS represents dimethyl-tert-butylsilyl group; or treating compound (4b) with ρ-nitrophenyl chloroformate to form a carbonate compound (5b), in which PMB represents ρ-methoxybenzyl group;

(v) treating compound (5a) with 4-ethynylaniline or 4-ethynylbenzylamine to form intermediate compounds (6a) and (6b), respectively; or treating compound (5b) with 4-ethynylaniline or 4-ethynylbenzylamine to form intermediate compounds (6c) and (6d), respectively;

(vi) treating compounds (6a) and (6b) with 7-azidoheptanoic acid in the presence of $Cu^+$ ion to form triazole compounds (7a) and (7b), respectively; or treating compounds (6c) and (6d) with 7-azidoheptanoic acid in the presence of $Cu^+$ ion to form triazole compounds (7c) and (7d), respectively;

(vii) activating acid compounds (7a) and (7b) followed by treatment with hydroxylamine to form hydroxamic acid compounds (8a) and (8b), respectively; or activating acid compounds (7c) and (7d) followed by treatment with hydroxylamine to form hydroxamic acid compounds (8c) and (8d), respectively; and (viii) removing the silyl group in compounds (8a) and (8b) with fluoride agent to form compounds (9a) and (9b), respectively.

In other embodiments, compounds of formula (III) can be prepared according to the following synthetic scheme 2.

Scheme 2

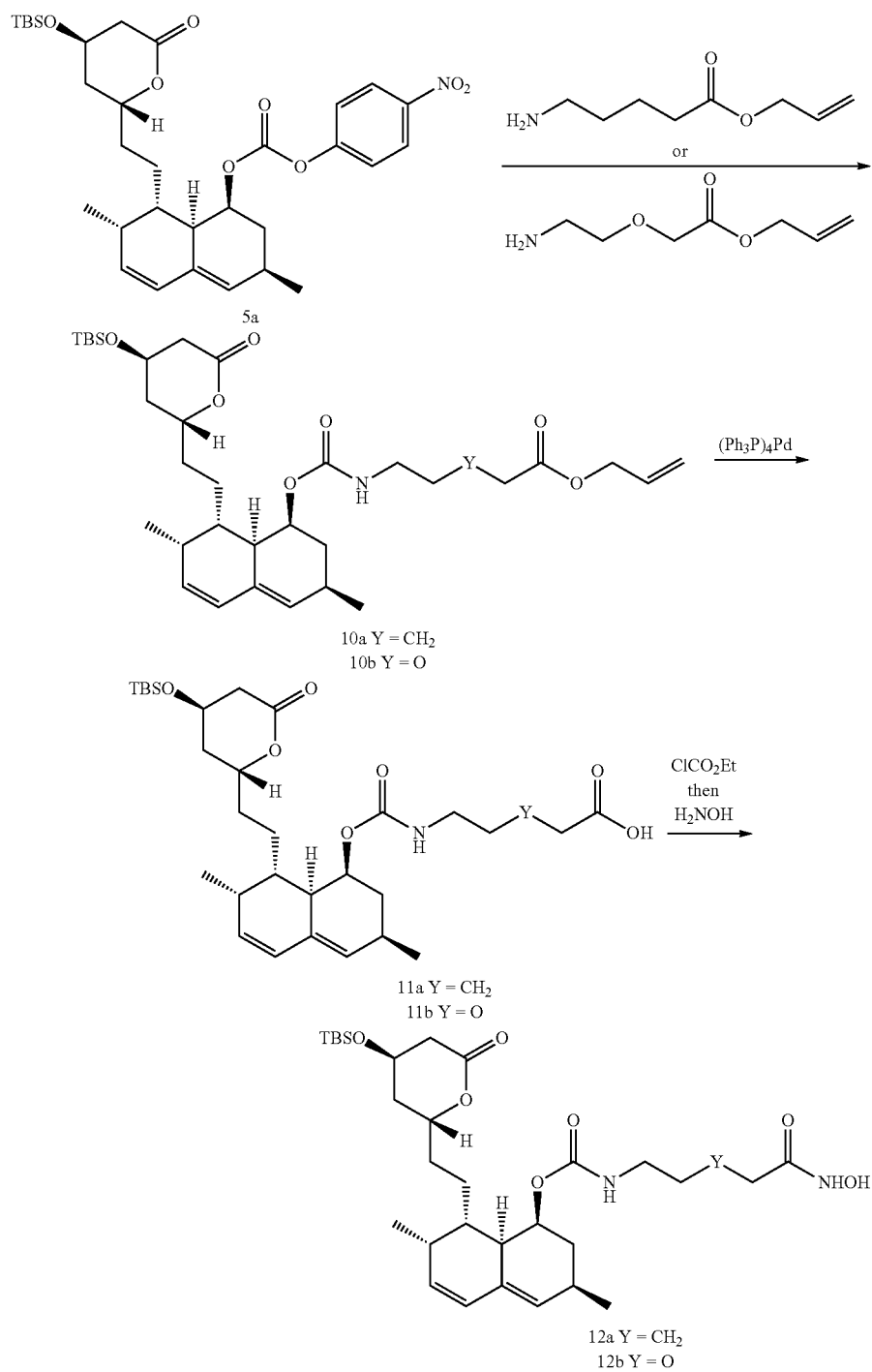

Specifically, the synthetic method as depicted in scheme 2 includes steps of:

(i) treating intermediate compound (5a) with 7-aminoheptanoic acid allyl ester or 5-amino-3-oxa-pentanoic acid to form compounds (10a) and (10b), respectively;

(ii) treating intermediate compound (10a) and (10b) with tetrakis(triphenylphosphine)palladium to form acid compounds (11a) and (11b), respectively; and (iii) activating acid compound (11a) and (11b) followed by treatment with hydroxylamine to form hydroxamic acids (12a) and (12b), respectively.

The second aspect of the present invention thus pertains to the method of treating an individual suffering from a disease or condition wherein inhibition or suppression of HDACs or HMGR provides a benefit comprising administering a therapeutically effective amount of a compound of formula (I) to an individual in need thereof.

The methods described herein relate to the use of a compound of formula (I), particularly the compound of formula (II) or (III) in the treatment of diseases and conditions wherein the suppression or inhibition of HDACs or HMGR provides a benefit. The methods of the present invention can be accomplished by administering a compound of formula (I) as the neat compound or as a pharmaceutical composition. Administration of a pharmaceutical composition, or near compound of formula (I), can be performed during or after the onset of the disease or condition of interest. Typically, the pharmaceutical compositions are sterile, and contain no toxic, carcinogenic, or mutagenic compounds that would cause an adverse reaction when administered.

As demonstrated below, a compound of formula (I) is a potent inhibitor of HDAC and HMGR and can be used in treating diseases and conditions wherein inhibition of HDAC and HMGR provides a benefit, for example, cancer, hypercholesterolemia, an acute or chronic inflammatory disease, autoimmune disease, allergic disease, pathogen infection, neurodegenerative disease, or a disease associated with oxidative stress.

In one embodiment, the invention provides a method for treating cancer comprising administering to a subject in need thereof an amount of a compound of formula (I) or a pharmaceutically acceptable salt thereof sufficient to treat the cancer. A compound of formula (I) can be used as the sole anticancer agent, or in combination with another anticancer treatment, e.g., radiation, chemotherapy, and surgery.

In another embodiment, the invention provides a method for treating cancer, said method comprising administering to a subject in need thereof a pharmaceutical composition comprising an amount of a compound of formula (I) effective to treat cancer. In a specific embodiment, the individual in need of treatment has previously undergone treatment for cancer. Such previous treatments include, but are not limited to, prior chemotherapy, radiotherapy, surgery, or immunotherapy, such as cancer vaccines.

In another embodiment, the cancer being treated is a cancer which has demonstrated sensitivity to radiotherapy and/or chemotherapy or is known to be responsive to radiotherapy and/or chemotherapy. Such cancers include, but are not limited to, Hodgkin's disease, Non-Hodgkin's lymphomas, Ewing's sarcoma, multiple myeloma, Wilms' tumor, bone tumors, neuroblastoma, retinoblastoma, testicular cancer, thyroid cancer, prostate cancer, larynx cancer, cervical cancer, nasopharynx cancer, breast cancer, colon cancer, pancreatic cancer, head and neck cancer, esophageal cancer, rectal cancer, small-cell lung cancer, non-small-cell lung cancer, brain cancer, melanoma, a non-melanoma skin cancer, and a CNS neoplasm.

The present disclosure thus pertains to a pharmaceutical composition for treating diseases and conditions wherein inhibition of HDAC and HMGR provides a benefit. In some embodiments, the compounds of the present disclosure (e.g., compound of formula (II) or (III)) may be formulated into pharmaceutical compositions by combining with appropriate pharmaceutically acceptable carriers or excipients, and may be formulated into solid, semi-solid, or liquid forms, such as tablets, capsules, powders, granules, ointments, solutions, suppositories, and injections. As such, administration of the active compound can be achieved in various ways, including oral, buccal, rectal, parental, intraperitoneal, and etc. administration. In pharmaceutical dosage forms, the active compound may be administered alone or in combination with other known pharmaceutically active agent to treat diseases and conditions wherein inhibition of HDAC and HMGR provides a benefit. One of skilled person in the art is familiar with the various dosage forms that are suitable for use in each route. It is to be noted that the most suitable route in any given case would depend on the nature or severity of the disease or condition being treated.

In some embodiments, the pharmaceutical compositions of this disclosure are solid dosage forms for oral administration. Such solid dosage forms may be capsules, sachets, tablets, pills, lozenges, powders or granules. In such forms, the active ingredient such as any of the compounds described above is mixed with at least one pharmaceutically acceptable excipient. Any of the described solid dosage forms may optionally contain coatings and shells, such as enteric coatings, and coatings for modifying the release rate of any of the ingredients. Examples of such coatings are well known in the art. In one example, the pharmaceutical compositions of this disclosure are tablets such as quick-release tablets. In still another example, the pharmaceutical compositions of this disclosure are formulated into sustained release forms. In another example, the pharmaceutical compositions of this disclosure are powders that are encapsulated in soft and hard gelatin capsules.

In some embodiments, the pharmaceutical compositions of the present disclosure are liquid dosage forms for oral administration. The liquid formulation may further include a buffering agent to maintain a desired pH. The liquid dosage formulations may also be filled into soft gelatin capsules. For example, the liquid may include a solution, suspension, emulsion, micro-emulsion, precipitate or any desired liquid media carrying any of the compound as described above, or a pharmaceutically acceptable derivative, salt or solvate thereof, or a combination thereof. The liquid may be designed to improve the solubility of active compound as described above to form a drug-containing emulsion or disperse phase upon release.

In some embodiments, the pharmaceutical compositions of this disclosure are formulations suitable for parenteral administration, such as administration by injection, which includes, but is not limited to, subcutaneous, bolus injection, intramuscular, intraperitoneal and intravenous injection. The pharmaceutical compositions may be formulated as isotonic suspensions, solutions or emulsions in oily or aqueous vehicles, and may contain formulatory agents such as suspending, stabilizing or dispersing agents. Alternatively, the compositions may be provided in dry form such as powders, crystallines or freeze-dried solids with sterile pyrogen-free water or isotonic saline before use. They may be presented in sterile ampoules or vials.

The following Examples are provided to elucidate certain aspects of the present invention and to aid those of skilled in the art in practicing this invention. These Examples are in no way to be considered to limit the scope of the invention in any manner. Without further elaboration, it is believed that one skilled in the art can, based on the description herein, utilize the present invention to its fullest extent. All publications cited herein are hereby incorporated by reference in their entirety.

EXAMPLE

Example 1

Synthesis of the Compounds of the Present Invention

1.1 Synthesis of Compound (4a)

(4R,6R)-6-[2-((1S,2S,6R,8S,8aR)-8-Hydroxy-2,6-dimethyl-1,2,6,7,8,8a-hexahydronaphthyl)ethyl]-4-tert-butyldimethylsilyloxy-3,4,5,6-tetrahydro-2H-pyran-2-one Lovastatin (1, 9.0 g, 22.3 mmol) was heated with potassium hydroxide (12.6 g, 224.5 mmol) in H$_2$O/MeOH (1:6, 63 mL) under reflux for 8 h. After adding H$_2$O (49.5 mL) to the mixture, MeOH was removed under reduced pressure to give compound (2). To compound (2), H$_2$O (180 mL), CH$_2$Cl$_2$ (45 mL), and 6 M HCl aqueous solution were added until pH reached 2. The mixture was stirred at room temperature for 4.5 h, and then neutralized with saturated NaHCO$_3$ aqueous solution. Extracted the mixture with CH$_2$Cl$_2$. The combined organic phase was dried over anhydrous MgSO$_4$, filtered and concentrated to give a deacylation product (3) as orange oil. TLC (EtOAc) R$_f$=0.33.

The crude product (3) was treated with tert-butyldimethylsilyl chloride (8.7 g, 57.9 mmol) and imidazole (8.8 g, 129.1 mmol) in CH$_2$Cl$_2$ (82 mL) at room temperature for 5.5 h. The mixture was concentrated under reduced pressure, and the residue was extracted with CH$_2$Cl$_2$ and H$_2$O. The organic phase was dried over MgSO$_4$, filtered, concentrated, and purified by flash chromatography (silica gel, EtOAc/hexane (2:8) to EtOAc) to give the compound (4a) (5.6 g, 58% overall yield from lovastatin).

C$_{25}$H$_{42}$O$_4$Si; white solid, mp 141.1-142.3° C.; TLC (EtOAc/hexane (6:4)) R$_f$=0.61; $^1$H NMR (CDCl$_3$, 400 MHz) δ 5.98 (1H, d, J=9.6 Hz), 5.78-5.82 (1H, m), 5.55 (1H, br s), 4.66-4.70 (1H, m), 4.29-4.30 (1H, m), 4.23-4.25 (1H, m), 2.54-2.65 (2H, m), 2.35-2.45 (2H, m), 2.16-2.18 (1H, m), 1.70-1.93 (7H, m), 1.44-1.55 (2H, m), 1.15 (3H, d, J=7.6 Hz), 0.88-0.91 (12H, m), 0.08 (6H, d, J=1.6 Hz); $^{13}$C NMR (CDCl$_3$, 100 MHz) 170.4, 133.6, 131.3, 129.9, 128.4, 76.3, 65.1, 63.5, 39.2, 38.7, 36.8, 36.3, 35.7, 32.9, 30.7, 27.3, 25.6 (3×), 24.2, 23.7, 17.9, 13.9, −5.0 (2×).

1.2 Synthesis of the Compound (5a)

(4R,6R)-6-(2-{(1S,2S,6R,8S,8aR)-8-[(p-Nitrophenoxy)carbonyloxy]-2,6-dimethyl-1,2,6,7,8,8a-hexahydronaphthyl}ethyl)-4-tert-butyldimethylsilyloxy-3,4,5,6-tetrahydro-2H-pyran-2-one The compound (4a) (5.0 g, 11.5 mmol), p-nitrophenyl chloroformate (16.2 g, 80.2 mmol) and dimethyl aminopyridine (DMAP) (98.0 g, 80.2 mmol) was mixed and stirred in anhydrous pyridine (80.2 mL) at room temperature for 15 h. Pyridine was removed under reduced pressure, and the residue was extracted with CH$_2$Cl$_2$ and 1 M HCl aqueous solution. The combined organic phase was washed with saturated NaHCO$_3$ aqueous solution and brine, dried over MgSO$_4$, filtered and concentrated under reduced pressure. The residue was purified by flash chromatography (silica gel, CH$_2$Cl$_2$/hexane (6:4 to 8:2)) to give the carbonate compound (5a) (5.6 g, 81%).

C$_{32}$H$_{45}$NO$_8$Si; white powder, mp 146.5-147.3° C.; [α]$^{25}_D$=+233.9 (EtOAc, c=1.0); TLC (EtOAc/hexane (2:8)) R$_f$=0.24; IR ν$_{max}$ (neat) 2955, 2930, 2857, 2360, 1760, 1594, 1525, 1347, 1258, 1216, 1082 cm$^{-1}$; $^1$H NMR (CDCl$_3$, 400 MHz) δ 8.27 (2H, d, J=9.2 Hz), 7.40 (2H, d, J=8.8 Hz), 6.01 (1H, d, J=9.6 Hz), 5.79-5.83 (1H, m), 5.57 (1H, br s), 5.34 (1H, br s), 4.68-4.70 (1H, m), 4.27-4.29 (1H, m), 2.52-2.59 (3H, m), 2.34-2.41 (2H, m), 2.17-2.23 (1H, m), 1.66-2.00 (6H, m), 1.45-1.53 (2H, m), 1.17 (3H, d, J=7.6 Hz), 0.93 (3H, d, J=6.8 Hz), 0.86 (9H, s), 0.06 (6H, d, J=5.6 Hz); $^{13}$C NMR (CDCl$_3$, 100 MHz) 170.2, 155.6, 152.3, 145.3, 133.2, 131.1, 129.3, 128.1, 125.2 (2×), 122.0 (2×), 75.4, 74.5, 63.6, 39.3, 37.5, 36.7, 36.1, 32.5, 32.2, 30.8, 27.3, 25.7 (3×), 23.5, 22.5, 17.9, 13.9, −4.9 (2×); ESI-HRMS calcd. for C$_{32}$H$_{46}$NO$_8$Si: 600.2993. found: m/z 600.3002 [M+H]$^+$.

1.3 Synthesis of Compound (6a)

(4R,6R)-6-(2-{(1S,2S,6R,8S,8aR)-8-[(4-ethynylphenyl)carbamoyloxy]-2,6-dimethyl-1,2,6,7,8,8a-hexahydronaphthyl}ethyl)-4-tert-butyldimethylsilyloxy-3,4,5,6-tetrahydro-2H-pyran-2-one The compound (5a) (1.5 g, 2.5 mmol), 4-ethynylaniline (2.1 g, 17.6 mmol) and DMAP (2.1 g, 17.6 mmol) were mixed in anhydrous pyridine (6.3 mL) and stirred at ambient temperature for 21 h. Pyridine was removed under reduced pressure, and the residue was extracted with CH$_2$Cl$_2$ and 1 M HCl aqueous solution. The combined organic phase was washed with saturated NaHCO$_3$ aqueous solution and brine, dried over MgSO$_4$, filtered and concentrated under reduced pressure. The residue was purified by flash chromatography (silica gel, EtOAc/hexane (15:85)) to give the carbamate compound (6a) (957 mg, 66%).

C$_{34}$H$_{47}$NO$_5$Si; orange oil; [α]$^{25}_D$=+213.9 (EtOAc, c=1.0); TLC (EtOAc/hexane (5:5)) R$_f$=0.66; IR ν$_{max}$ (neat) 3299, 2955, 2858, 1734, 1591, 1523, 1313, 1255, 1219, 1082, 1047, 839 cm$^{-1}$; $^1$H NMR (CDCl$_3$, 400 MHz) δ 7.41 (4H, s), 7.00 (1H, s), 6.00 (1H, d, J=9.6 Hz), 5.79-5.83 (1H, m), 5.56 (1H, br s), 5.32 (1H, br s), 4.62-4.63 (1H, m), 4.18-4.20 (1H, m), 3.01 (1H, s), 2.46-2.52 (3H, m), 2.29-2.39 (2H, m), 2.17-2.21 (1H, m), 1.53-1.96 (6H, m), 1.39-1.43 (2H, m), 1.10 (3H, d, J=7.6 Hz), 0.91 (3H, d, J=6.8 Hz), 0.86 (9H, s), 0.05 (6H, d, J=3.6 Hz); $^{13}$C NMR (CDCl$_3$, 100 MHz) 170.6, 153.1, 138.8, 133.4, 132.9 (2×), 131.9, 129.6, 128.1, 118.0 (2×), 116.4, 83.5, 76.3, 75.6, 69.6, 63.5, 39.2, 37.3, 36.6, 36.3, 32.5, 32.4, 30.8, 27.4, 25.6 (3×), 23.4, 22.6, 17.9, 13.9, −5.0 (2×); ESI-HRMS (negative mode) calcd. for C$_{34}$H$_{46}$NO$_5$Si: 576.3145. found: m/z 576.3131 [M−H]$^-$.

1.4 Synthesis of Compound (6b)

(4R,6R)-6-(2-{(1S,2S,6R,8S,8aR)-8-[(4-Ethynylbenzyl)carbamoyloxy]-2,6-dimethyl-1,2,6,7,8,8a-hexahydronaphthyl}ethyl)-4-tert-butyldimethylsilyloxy-3,4,5,6-tetrahydro-2H-pyran-2-one The compound (5a) (500 mg, 0.8 mmol), 4-ethynylbenzylamine hydrochloride (419 mg, 2.5 mmol) and DMAP (712 mg, 5.8 mmol) were mixed and stirred in anhydrous pyridine (2 mL) at ambient temperature for 3 h. Pyridine was removed under reduced pressure, and the residue was extracted with CH$_2$Cl$_2$ and 1 M HCl aqueous solution. The combined organic phase was washed with saturated NaHCO$_3$ aqueous solution and brine, dried over MgSO$_4$, filtered and concentrated under reduced pressure. The residue was purified by flash chromatography (silica gel; EtOAc/hexane (2:8)) to give the carbamate compound (6b) (444 mg, 90%).

C$_{35}$H$_{49}$NO$_5$Si; colorless oil; [α]$^{25}_D$=+217.6 (EtOAc, c=1.0); TLC (EtOAc/hexane (5:5)) R$_f$=0.57; IR ν$_{max}$ (neat)

3306, 2955, 2829, 2857, 1727, 1509, 1461, 1359, 1259, 1081, 1044, 1016, 924, 837, 778 cm$^{-1}$; $^1$H NMR (CDCl$_3$, 400 MHz) δ 7.42 (2H, d, J=8.0 Hz), 7.22 (2H, d, J=8.0 Hz), 5.97 (1H, d, J=9.6 Hz), 5.75-5.79 (1H, m), 5.52 (1H, br s), 5.31 (1H, br s), 5.22 (1H, br s), 4.61 (1H, br s), 4.30-4.41 (2H, m), 4.23 (1H, br s), 3.05 (1H, s), 2.54 (2H, br s), 2.43 (1H, br s), 2.12-2.36 (3H, m), 1.78-1.90 (4H, m), 1.24-1.54 (4H, m), 1.09 (3H, d, J=7.2 Hz), 0.87-0.91 (12H, m), 0.07 (6H, d, J=2.8 Hz); $^{13}$C NMR (CDCl$_3$, 100 MHz) 170.5, 156.4, 140.0, 133.3, 132.2 (2×), 131.9, 129.6, 128.2, 127.2 (2×), 120.8, 83.3, 76.7, 75.5, 68.9, 63.6, 44.4, 39.3, 37.3, 36.5, 36.2, 32.6, 30.9, 27.4, 25.6 (3×), 23.2, 22.6, 17.9, 13.9, −4.9 (2×); ESI-HRMS calcd. for C$_{35}$H$_{50}$NO$_5$Si: 592.3458. found: m/z 592.3458 [M+H]$^+$.

1.5 Synthesis of Compound (8a)

(4R,6R)-6-(2-{(1S,2S,6R,8S,8aR)-8-[(4-{1-[7-(Hydroxyamino)-7-oxoheptyl]-1H-1,2,3-triazol-4-yl}phenyl)carbamoyloxy]-2,6-dimethyl-1,2,6,7,8,8a-hexahydronaphthyl}ethyl)-4-tert-butyldimethylsilyloxy-3,4,5,6-tetrahydro-2H-pyran-2-one A mixture of the compound (6a) (827 mg, 1.4 mmol), CuSO$_4$.5H$_2$O (71 mg, 0.29 mmol), sodium ascorbate (168 mg, 0.85 mmol) and 7-azidoheptanoic acid (245 mg, 1.4 mmol) in H$_2$O/t-BuOH (1:1, 19 mL) was stirred at 60° C. for 18 h. The mixture was concentrated under reduced pressure, and the residue was extracted with EtOAc and H$_2$O. The organic phase was dried over MgSO$_4$, filtered, and concentrated to give a practically pure 1,3-cycloaddition product (7a). C$_{41}$H$_{60}$N$_4$O$_7$Si; colorless oil; TLC (EtOAc/hexane (7:3)) R$_f$=0.11.

The above-prepared compound (7a) was treated with ethyl chloroformate (0.4 mL, 4.3 mmol) and Et$_3$N (0.8 mL, 5.7 mmol) in anhydrous THF (4.3 mL) at 0° C. for 10 min. A solution of hydroxylamine, freshly prepared by neutralization of hydroxylamine hydrochloride (497 mg, 7.2 mmol) with KOH (360 mg, 6.4 mmol) in anhydrous MeOH (2 mL), was added. The mixture was stirred at 0° C. for another 15 min, and concentrated under reduced pressure. The residue was extracted with EtOAc and H$_2$O. The organic phase was dried over MgSO$_4$, filtered, and concentrated to yield an pale orange oil, which was purified by flash chromatography (silica gel, CH$_2$Cl$_2$/MeOH (15:1 to 9:1)) to give hydroxamic acid (8a) (404 mg, 37% overall yield). The purity of compound (8a) was 98% as shown by HPLC analysis on an HC-C18 column (Agilent, 4.6×250 mm, 5 μm), t$_R$=17.9 min (gradients of 55-100% aqueous CH$_3$CN in 30 min).

C$_{41}$H$_{61}$N$_5$O$_7$Si; colorless oil; [α]$^{24}_D$=+129.1 (EtOAc, c=1.0); IR v$_{max}$ (neat) 3287, 2929, 2857, 1734, 1662, 1596, 1531, 1460, 1359, 1313, 1221, 1081, 1047, 837, 779 cm$^{-1}$; $^1$H NMR (CDCl$_3$, 400 MHz) δ 7.73 (3H, m), 7.50 (2H, d, J=7.2 Hz), 7.12 (1H, br s), 6.00 (1H, d, J=9.6 Hz), 5.79-5.83 (1H, m), 5.56 (1H, br s), 5.33 (1H, br s), 4.64 (1H, br s), 4.35 (2H, br s), 4.19 (1H, br s), 2.30-2.50 (5H, m), 2.12-2.20 (3H, m), 1.26-1.96 (16H, m), 1.11 (3H, d, J=7.6 Hz), 0.91 (3H, d, J=7.2 Hz), 0.85 (9H, s), 0.04 (6H, s); $^{13}$C NMR (CDCl$_3$, 100 MHz) 170.8, 153.4, 147.5, 138.3, 133.5, 131.9, 129.8, 128.2, 126.4 (2×), 125.4, 119.2, 118.8 (2×), 77.2, 75.8, 69.6, 63.6, 50.0, 39.3, 37.4, 36.5, 36.4, 32.6, 32.4, 30.9, 29.8, 27.8, 27.5, 25.7 (3×), 25.5, 24.8, 23.4, 22.7, 17.9, 14.0, −4.9 (2×); ESI-HRMS calcd. for C$_{41}$H$_{62}$N$_5$O$_7$Si: 764.4419. found: m/z 764.4423 [M+H]$^+$.

1.6 Synthesis of Compound (8b)

(4R,6R)-6-(2-{(1S,2S,6R,8S,8aR)-8-[(4-{1-[7-(Hydroxyamino)-7-oxoheptyl]-1H-1,2,3-triazol-4-yl}benzyl)carbamoyloxy]-2,6-dimethyl-1,2,6,7,8,8a-hexahydronaphthyl}ethyl)-4-tert-butyldimethylsilyloxy-3,4,5,6-tetrahydro-2H-pyran-2-one By a procedure similar to that of example 1.5, the 1,3-dipolar cycloaddition product (7b) obtained from compound (6b) (734 mg, 1.2 mmol) and 7-azidoheptanoic acid (202 mg, 1.2 mmol) was activated with ethyl chloroformate, and then reacted with hydroxylamine (6.2 mmol) in MeOH (1.7 mL) to give hydroxamic acid (8b) (511 mg, 53% overall yield). The purity of product (8b) was 98% as shown by HPLC analysis on an HC-C18 column (Agilent, 4.6×250 mm, 5 μm), t$_R$=17.4 min (gradients of 55-100% aqueous CH$_3$CN in 30 min).

C$_{42}$H$_{63}$N$_5$O$_7$Si; colorless oil; [α]$^{23}_D$=+171.9 (EtOAc, c=1.0); IR v$_{max}$ (neat) 3291, 2952, 2829, 2857, 1719, 1668, 1519, 1460, 1360, 1259, 1080, 1044, 836, 778 cm$^{-1}$; $^1$H NMR (CDCl$_3$, 400 MHz) δ 7.76 (3H, m), 7.31 (2H, d, J=7.6 Hz), 5.98 (1H, d, J=9.6 Hz), 5.76-5.80 (1H, m), 5.53 (1H, br s), 5.35 (1H, br s), 5.27 (1H, br s), 4.59-4.61 (1H, m), 4.30-4.47 (4H, m), 4.17 (1H, br s), 2.09-2.46 (8H, m), 1.19-1.94 (16H, m), 1.11 (3H, d, J=7.2 Hz), 0.86-0.90 (12H, m), 0.05 (6H, s); $^{13}$C NMR (CDCl$_3$, 100 MHz) 171.0, 156.5, 147.3, 139.2, 133.3, 131.9, 129.8, 129.5, 128.2 (2×), 127.6, 125.8 (2×), 119.8, 77.2, 76.0, 68.8, 63.5, 50.1, 44.4, 39.2, 37.3, 36.5, 36.0, 32.7, 31.0, 29.8, 29.7, 27.8, 27.5, 25.7 (3×), 25.6, 24.8, 23.1, 22.7, 17.9, 14.0, −4.9 (2×); ESI-HRMS calcd. for C$_{42}$H$_{64}$N$_5$O$_7$Si: 778.4575. found: m/z 778.4584 [M+H]$^+$.

1.7 Synthesis of Compound (10a)

(4R,6R)-6-[2-((1S,2S,6R,8S,8aR)-8-{[7-(Allyloxy)-7-oxoheptyl]carbamoyloxy}-2,6-dimethyl-1,2,6,7,8,8a-hexahydronaphthyl)ethyl]-4-tert-butyldimethylsilyloxy-3,4,5,6-tetrahydro-2H-pyran-2-one By a procedure similar to example 1.3, the compound (5a) (354 mg, 0.6 mmol) was treated with allyl 7-aminohepanoate (as the hydrochloric salt, 393 mg, 0.78 mmol) and DMAP (505 mg, 4.1 mmol) in anhydrous pyridine (1.5 mL) at ambient temperature for 2 h to give carbamate compound (10a) (267 mg, 70% yield).

C$_{36}$H$_{59}$NO$_7$Si; colorless oil; [α]$^{23}_D$=+174.5 (EtOAc, c=1.0); TLC (EtOAc/hexane (1:1)) R$_f$=0.57; IR v$_{max}$ (neat) 3369, 2930, 2857, 1742, 1520, 1462, 1339, 1253, 1082, 926, 837, 778 cm$^{-1}$; $^1$H NMR (CDCl$_3$, 400 MHz) δ 5.98 (1H, d, J=9.6 Hz), 5.88-5.95 (1H, m), 5.76-5.80 (1H, m), 5.52 (1H, br s), 5.32 (1H, d, J=17.2 Hz), 5.23 (1H, d, J=10.4 Hz), 5.18 (1H, br s), 4.79 (1H, br s), 4.63-4.66 (1H, m), 4.57 (2H, d, J=5.6 Hz), 4.28-4.29 (1H, m), 3.20-3.23 (1H, m), 3.05-3.10 (1H, m), 2.56-2.63 (2H, m), 2.09-2.42 (6H, m), 1.26-1.88 (16H, m), 1.08 (3H, d, J=7.2 Hz), 0.88-0.90 (12H, m), 0.08 (6H, s); $^{13}$C NMR (CDCl$_3$, 100 MHz) 173.2, 171.5, 156.3, 133.3, 132.2, 132.0, 129.6, 128.2, 118.0, 75.8, 68.4, 64.9, 63.6, 40.7, 39.3, 37.3, 36.6, 36.3, 34.0, 32.6, 32.5, 30.9, 29.7, 28.6, 27.4, 26.2, 25.6 (3×), 24.7, 22.5, 19.7, 13.9, −5.0 (2×); ESI-HRMS calcd. for C$_{36}$H$_{60}$NO$_7$Si: 646.4139. found: m/z 646.4142 [M+H]$^+$.

1.8 Synthesis of Compound (12a)

(4R,6R)-6-[2-((1S,2S,6R,8S,8aR)-8-{[7-(Hydroxyamino)-7-oxoheptyl]carbamoyloxy}-2,6-dimethyl-1,2,6,7,8,8a-hexahydronaphthyl)ethyl]-4-tert-butyldimethylsilyloxy-3,4,5,6-tetrahydro-2H-pyran-2-one A mixture of the compound (10a) (268 mg, 0.4 mmol), tetrakis(triphenylphosphine)palladium (48 mg, 0.04 mmol), triphenylphosphine (22 mg, 0.08 mmol), triethylamine (0.17 mL, 1.2 mmol) and formic acid (0.047 mL, 1.2 mmol) in degassed THF (2 mL) was stirred at ambient temperature for 3 h. The mixture was concentrated under reduced pressure. $CH_2Cl_2$ and $H_2O$ were added, and the mixture was acidified with 1 M HCl aqueous solution to pH=2. The mixture was extracted with $CH_2Cl_2$. The combined organic phase was dried over $MgSO_4$, filtered, concentrated and separated by flash chromatography (silica gel, $CH_2Cl_2$/MeOH (17:1)) to give a carboxylic acid product (11a) as colorless oil.

By a procedure similar to that for compound (8a), the above-prepared carboxylic acid (11a) was activated with ethyl chloroformate and reacted with hydroxylamine (2.1 mmol) in MeOH (0.6 mL) to give hydroxamic acid (12a) (98 mg, 38% overall yield). The purity of product (12a) was 97% as shown by HPLC analysis on an HC-C18 column (Agilent, 4.6×250 mm, 5 μm), $t_R$=15.2 min (gradients of 60-100% aqueous $CH_3CN$ in 30 min). $C_{33}H_{56}N_2O_7Si$; colorless oil; $[\alpha]^{26}_D$=+132.2 (EtOAc, c=1.0); IR $v_{max}$ (neat) 3288, 2929, 2857, 1713, 1522, 1462, 1359, 1255, 1081, 1046, 837, 778 $cm^{-1}$; $^1H$ NMR ($CDCl_3$, 400 MHz) δ 5.98 (1H, d, J=9.6 Hz), 5.76-5.80 (1H, m), 5.52 (1H, br s), 5.19 (1H, br s), 4.88 (1H, br s), 4.68 (1H, br s), 4.30 (1H, br s), 3.15-3.16 (2H, m), 2.53-2.66 (2H, m), 2.08-2.42 (6H, m), 1.26-1.89 (16H, m), 1.08 (3H, d, J=7.2 Hz), 0.89 (12H, m), 0.08 (6H, s); $^{13}C$ NMR ($CDCl_3$, 100 MHz) 171.1, 171.0, 156.5, 133.2, 131.9, 129.6, 128.2, 77.2, 68.4, 63.4, 40.5, 39.2, 37.3, 36.2, 36.1, 32.5, 32.3, 30.9, 29.5, 28.2, 27.3, 25.9, 25.6 (3×), 25.0, 23.0, 22.5, 17.8, 13.8, −5.0 (2×); ESI-HRMS calcd. for $C_{33}H_{57}N_2O_7Si$: 621.3935. found: m/z 621.3922 $[M+H]^+$.

Example 2

Inhibitory Effects of the Compounds of Example 1 on HMGR and HDAC

In this example, the effects of the compounds of example 1, particularly compounds 8a, 8b, and 12a on respective activities of HMGR and HDAC were determined by in vitro enzyme assays and cell-base HMG-CoA assay. Results are summarized in Tables 1 and 2, as well as in FIG. 1.

Cell Culture.

Human lung carcinoma cell line A549 was obtained from American Type Culture Collection (ATCT) (Manassas, Va.). A549 cells were cultured in Dulbecco's modified Eagle's medium (DMEM) in a humidified incubator containing 5% $CO_2$/95% air.

HDAC Activity Assay.

The HDAC activity was performed using the HDAC fluorescent activity assay kit (BIOMOL, Plymouth Meeting, Pa., USA) according to the manufacturer's instructions. Briefly, recombinant proteins of HDAC1 or HDAC6 were incubated with test compounds, and HDAC reaction was initiated by addition of Fluor-de-Lys substrate. Samples were incubated for 10 min at room temperature, followed by adding developer to stop the reaction. Fluorescence was measured by fluorometric reader with excitation at 360 nm and emission at 460 nm. The HDAC activity was expressed as arbitrary fluorescence units (AFU). The HDAC activity was calculated as a percentage of activity compared with the control group. The half maximal inhibitory concentration ($IC_{50}$) values for the test compounds were calculated from software SigmaPlot.

HMG-CoA Reductase (HMGR) Activity Assay.

The HMGR activity was performed using HMG-CoA reductase assay kit from Sigma-Aldrich with the human recombinant protein or 100 μg total cell lysates from A549 cells. Lovastatin was used as a positive control, and SAHA as a negative control. HMGR activity under defined assay conditions, containing NADPH and HMG-CoA substrate in a final volume of 0.2 mL of 100 mM potassium phosphatate buffer (120 mM KCl, 1 mM EDTA, 5 mM DTT, pH 7.4), were initiated in the presence or absence (control) of test compounds dissolved in dimethylsulfoxide (DMSO). The rates of NADPH consumption were monitored every 20 seconds, for up to 10 minutes, by spectrophotometer at 37° C. and 340 nm. The HMGR activity was calculated as a percentage of activity compared with the control group at 5 min. The $IC_{50}$ values were calculated from software SigmaPlot.

Western Blot Analysis.

After treated with test compounds (i.e., compounds of example 1), cells were lysed on ice, and cell lysates were collected and subjected to SDS-PAGE. Immunoblotting was performed using specific antibodies to evaluate the expression of proteins.

TABLE 1

Inhibitory Activities ($IC_{50}$) Against HMGR and HDACs

| | $IC_{50}$ (nM) | | | |
|---|---|---|---|---|
| compound | HMGR | HDAC1 | HDAC2 | HDAC6 |
| lovastatin | 29.5 ± 3.5[a] | 11911 ± 681[a] | 25933 ± 651[a] | 16285 ± 1575[a] |
| SAHA | ND[b] | 20.9 ± 7.1[a] | 100.9 ± 10.0[a] | 19.4 ± 6.0[a] |
| 6a | 36.5 ± 5.3 | 159.0 ± 8.4 | 463.3 ± 28.0 | 127.4 ± 21.5 |
| 6b | 53.8 ± 5.2 | 124.7 ± 6.3 | 881.8 ± 9.7 | 34.0 ± 4.3 |
| 8a | 36.5 ± 5.3[a] | 159.0 ± 8.4[a] | 463.3 ± 28.0[a] | 127.4 ± 21.5[a] |
| 8b | 53.8 ± 5.2[a] | 124.7 ± 6.3[a] | 881.8 ± 9.7[a] | 34.0 ± 4.3[a] |
| 12a | 54.1 ± 2.1[a] | 122.0 ± 12.7[a] | 657.7 ± 21.1[a] | 139.7 ± 5.7[a] |

[a]Data are presented as mean ± SD of three experiments.
[b]ND: not determined (>10 μM).

As evident from the results summarized in Table 1, compounds 8a, 8b, and 12a inhibited HMGR with $IC_{50}$ values in nanomolar range similar to that of lovastatin. In contrast, SAHA had no inhibition on HMGR activity at any dose. Lovastatin failed to exhibit significant inhibition against HDAC1 (class I), HDAC2 (class I) or HDAC6 (class II), whereas compounds 8a, 8b and 12a inhibited both classes of HDACs with $IC_{50}$ values in sub-micromolar range. These results clearly indicated that compounds 8a, 8b and 12a acted as potent dual functional inhibitors against HMGR and HDACs.

The intracellular histone acetylation status is a direct indicator for class I HDAC inhibition, whereas α-tubulin is the substrate of class II HDAC (i.e., HDAC 6). Western blot analysis indicated that a known HDAC inhibitor, SAHA (suberanilohydroxamic acid), at 5 μM markedly induced acetylation of histone and tubulin, whereas lovastatin had no effect. As to compounds 8a and 8b, both compounds promoted histone and tubulin acetylation in a dose dependent manner (FIG. 1).

To further evaluate the effects of compounds of example 1 on HMGR in lung cancer cells, compounds 8a, 8b and 12a at indicated doses of 1-50 μM were applied to cells for 24 h, and the HMGR activity in whole cell lysates was measured. As summarized in Table 2, compounds 8a, 8b and 12a effectively reduced HMGR activity in a dose-dependent manner similar to lovastatin. However, SAHA failed to inhibit HMGR at any dose.

TABLE 2

Inhibition on the HMGR activity in A549 lung cancer cells.

| | Compound | | | | |
|---|---|---|---|---|---|
| | lovastatin | SAHA | 8a | 8b | 12a |
| IC$_{50}$ (μM) | 19.8 ± 2.2[a] | ND[b] | 22.3 ± 5.9[a] | 16.1 ± 4.8[a] | 13.2 ± 5.1[a] |

[a]Data are shown as mean ± SD of three experiments.
[b]ND: not determined (>10 μM) due to high toxicity of SAHA to cells.

It will be understood that the above description of embodiments is given by way of example only and that various modifications may be made by those with ordinary skill in the art. The above specification, examples, and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

What is claimed is:

1. A compound, and its pharmaceutically acceptable salt, solvate, or prodrug, in which the compound is selected from the group consisting of:

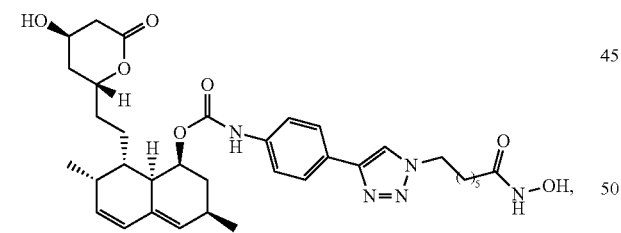

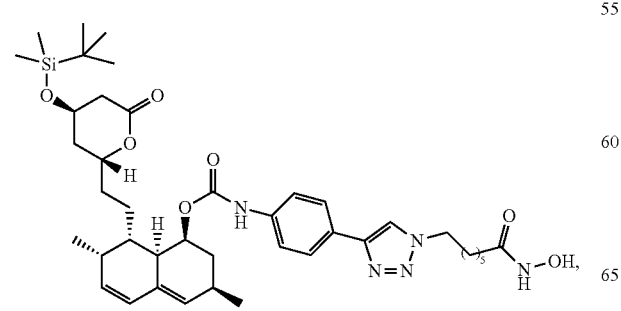

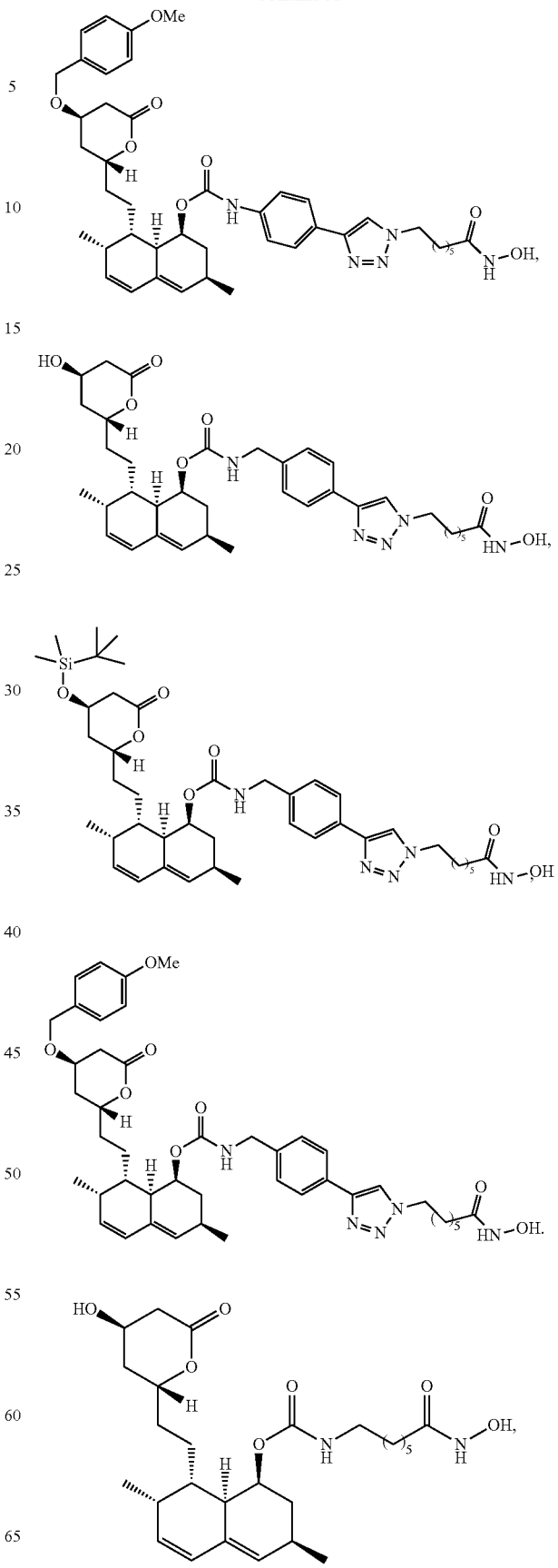

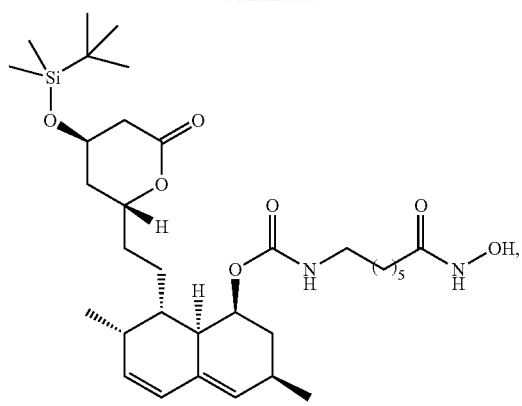
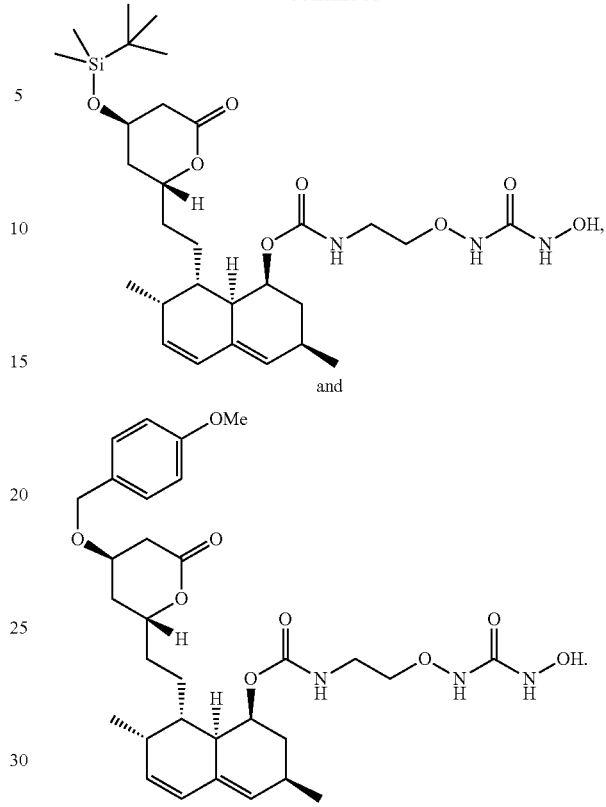
2. A pharmaceutical composition for treating diseases and conditions in which inhibition of histone deacetylase (HDAC) and 3-hydroxy-3-methylglutaryl coenzyme A (HMG Co-A) reductase (HMGR) provides a benefit comprising an effective amount of the compound of claim 1; and a pharmaceutically acceptable carrier.
* * * * *